US00PP10194P

United States Patent [19]

Anderson

[11] Patent Number: Plant 10,194

[45] Date of Patent: Jan. 13, 1998

[54] BRACHYCOME PLANT NAMED 'STRAWBERRY MOUSSE'

[75] Inventor: Richard Colin Anderson, Merricks, Australia

[73] Assignee: Koala Blooms Pty. Ltd., Victoria, Australia

[21] Appl. No.: 695,647

[22] Filed: Aug. 12, 1996

[51] Int. Cl.[6] ..... A01H 5/00

[52] U.S. Cl. ..... Plt./68.1

[58] Field of Search ..... Plt./68.1

[56] References Cited

PUBLICATIONS

GTITM Upovrom Listing for AUPBR 93/103 for Strawberry Mousse' on application filed Apr. 15, 1993.

*Primary Examiner*—James R. Feyrer
*Attorney, Agent, or Firm*—C. A. Whealy

[57] ABSTRACT

A new and distinct Brachycome named 'Strawberry Mousse', characterized by its low-growing and spreading plant habit; fast crop time; moderate vigor; freely branching plant habit; relatively large inflorescences with pink ray florets and bright yellow-green disc florets; and long, erect peduncles that hold inflorescences above the foliage.

1 Drawing Sheet

The present invention relates to a new and distinct cultivar of Brachycome plant, botanically known as a Brachycome hybrid and referred to by the cultivar name 'Strawberry Mousse'.

The new cultivar originated from a cross made by the inventor of *Brachycome angustifolia*, as the male or pollen parent, with *Brachycome formosa*, as the female or seed parent. The cultivar 'Strawberry Mousse' was discovered and selected by the inventor as a flowering plant within the progeny of the stated cross in a controlled environment in Merricks, Victoria, Australia. While the plant of this disclosure has been denominated 'Strawberry Mousse' for purposes of international recognition, it is contemplated that this plant will be sold under the trademark "Billabong" as "Billabong" 'Strawberry Mousse' in the United States.

Asexual reproduction of the new cultivar by terminal cuttings taken in a controlled environment in Merricks, Victoria, Australia, has shown that the unique features of this new Brachycome are stable and are reproduced true to type in successive propagations.

The new cultivar has not been observed under all possible environmental conditions. The phenotype may vary somewhat with variations in environment such as temperature, daylength and light intensity, without, however, any variance in genotype.

Compared to the parent cultivar *Brachycome angustifolia*, plants of the new Brachycome have larger leaves and larger inflorescences. Compared to the parent cultivar *Brachycome formosa*, plants of the new Brachycome are faster in growth rate, more vigorous, have longer peduncles, have pink rather than purple ray florets, and the adaxial surface of young leaves is green rather than dark purple. A detailed comparison of the differences between *Brachycome formosa* and the cultivar 'Strawberry Mousse' appears in Chart A at the end of the specification.

The new Brachycome can also be compared to the cultivar Pink Swirl which is thought to have the same parents as the new Brachycome. In side-by-side comparisons conducted in Merricks, Victoria, Australia, under commercial conditions, plants of the new Brachycome are more vigorous, ray floret color is paler pink, and the adaxial surface of the leaves is green rather than purple.

The following characteristics have been repeatedly observed and are determined to be basic characteristics of 'Strawberry Mousse' which distinguish 'Strawberry Mousse', as a new and distinct cultivar:

1. Low-growing and spreading plant habit.
2. Fast crop time.
3. Moderate vigor.
4. Freely branching plant habit.
5. Relatively large inflorescences with pink ray florets and bright yellow-green disc florets.
6. Long, erect peduncles that hold inflorescences above the foliage.

BRIEF DESCRIPTION OF THE VIEWS OF THE DRAWING

The accompanying colored photographs illustrate the overall appearance of the new cultivar, showing the colors as true as it is reasonably possible to obtain in colored reproductions of this type.

The first photograph, at the top, comprises a top perspective view of a single potted plant of 'Strawberry Mousse'.

The second photograph comprises a close-up view of inflorescences of plants of 'Strawberry Mousse'. Floret color in the photographs may appear different from the actual floret color due to light reflectance.

The following observations, measurements, values, and comparisons describe plants grown in Merricks, Victoria, Australia, under outdoor conditions with day temperatures ranging from 10 to 30C, night temperatures ranging from 5 to 20C, and light levels ranging from 5,000 to 9,000 foot-candles. Color references are made to The Royal Horticultural Society Colour Chart except where general terms of ordinary dictionary significance are used.

DETAILED BOTANICAL DESCRIPTION

CLASSIFICATION:

*Botanical.*—Brachycome hybrid cultivar 'Strawberry Mousse'.

*Commercial.*—Brachycome.

PARENTAGE:

*Male or pollen parent.*—Brachycome angustifolia.

*Female or seed parent.*—Brachycome formosa.

Propagation:

*Type.*—By cuttings.

*Time to initiate and develop roots.*—Summer: 10 to 20 days at temperatures of 25C. Winter: 15 to 30 days at temperatures of 20C.

*Rooting habit.*—Fibrous and freely branching.

it description:

*General appearance.*—Low-growing, spreading, herbaceous plant with spatulate fan-shaped foliage and erect flower stems. Appropriate for 12.5 pots to 25-cm hanging basket containers. To produce a 15-cm finished flowering plant from rooted cuttings, 8 to 12 weeks are required depending on temperature and light level.

Plant height: 11 to 14 cm from soil level to top of inflorescences.

*Branching:* Freely branching, typically 2 to 5 lateral branches develop when the terminal apex is removed (pinched). Lateral branches are typically 3 to 5.5 cm in length.

*Growth rate.*—Moderate.

*Vigor.*—Moderate

*Foliage description.*—Arrangement: Alternate, single. Quantity: 12 to 20 per lateral branch. Leaf shape: Spatulate. fan-shaped. Leaf apex: Trilobate. Leaf base: Cuneate, attenuate. Leaf margin: Deeply lobed. Leaf aspect: Flat. Leaf length: 2.5 to 4.5 cm. Leaf width: 1.5 to 2.5 cm. Leaf texture: Smooth, glabrous. Leaf attachment: Sessile. Leaf color: Young and fully expanded leaves: Abaxial surface: 137A. Adaxial surface: 138A. Venation: Abaxial surface: 137A. Adaxial surface: 138B.

vering description:

*Inflorescence.*—Single daisy-type composite inflorescence form. Florets arranged acropetally on a capitulum. Inflorescences last on the plant for 3 to 4 weeks and about 1 week as a fresh cut flower. Inflorescences semi-persistent.

*Natural flowering season.*—Natural flowering season is spring to fall. Plants flower continuously during this period.

*Quantity of inflorescences.*—One per lateral branch.

*Inflorescence diameter.*—2.8 to 3.8 cm.

*Inflorescence depth (height).*—About 1 cm.

*Fragrance.*—Not detectable.

*Ray florets.*—Quantity: 18 to 24 florets per inflorescence. Shape: Lanceolate. Apex: Acute. Margin: Entire. Length: About 1.5 cm. Width: 2 to 3 mm. Texture: Smooth, glabrous. Color: When opening, abaxial surface: 73B. Mature, abaxial surface: 73B, with further development, florets darken to 78B. Mature, adaxial surface: 65C.

*Disc florets.*—Shape: Tubular. Diameter of disc: 6 to 9 mm. Disc floret length: 3 to 4 mm. Disc floret width: About 1 mm. Color: Immature: 154C. Mature: 154B. Number of disc florets per inflorescence: Numerous.

*Peduncle.*—Length: About 9.2 cm. Strength: Moderately strong, inflorescences held erect above foliage. Texture: Smooth, glabrous. Color: 139A.

*Flower bud.*—Shape: Globular. Length: About 5 mm. Diameter: 4 to 5 mm. Color: 139C.

*Involucral bracts.*—Arrangement: Imbricated. Quantity: 16 to 20 per inflorescence. Shape: Elliptic to oblong. Apex: Obtuse. Margin: Ciliate. Texture: Smooth, glabrous. Color: Abaxial surface: 143C. Adaxial surface: 143C.

*Androecium.*—Stamen number: Five per floret. Anther shape: Linear. Anther length: About 1 mm. Pollen color: 155A.

*Gynoecium.*—Pistil number: One per floret. Stigma shape: Bilobate. Style length: About 2 mm.

Disease resistance: No susceptibility nor resistance to fungal, bacterial or viral pathogens has been noted.

Seed production: Seed production is typically not observed.

CHART A

| CHARACTERISTIC | Strawberry MOUSSE' | *Braehycome formosa* |
|---|---|---|
| PLANT HEIGHT | 11 to 14 cm | 2 to 15 cm |
| GROWTH RATE | Moderate | Slow |
| VIGOR | Moderate | Low |
| LATERAL BRANCH LENGTH | 3 to 5.5 cm | 4 to 8.5 cm |
| LEAF COLOR, YOUNG LEAVES, ABAXIAL SURFACE | 137A | 139A |
| LEAF COLOR, YOUNG LEAVES, ADAXIAL SURFACE | 138A | 83A |
| LEAF COLOR, MATURE LEAVES, ABAXIAL SURFACE | 137A | 137A |
| LEAF COLOR, MATURE LEAVES, ADAXIAL SURFACE | 138B | 138B |
| RAY FLORET COLOR, OPENING | 73B | 78C |
| RAY FLORET COLOR, MATURE ABAXIAL SURFACE | 73B | 78A |
| RAY FLORET COLOR, MATURE ADAXIAL SURFACE | 65C | 78C |
| PEDUNCLE LENGTH | About 9.2 cm | About 8.3 cm |

It is claimed:

1. A new and distinct Brachycome plant named 'Strawberry Mousse', as illustrated and described.

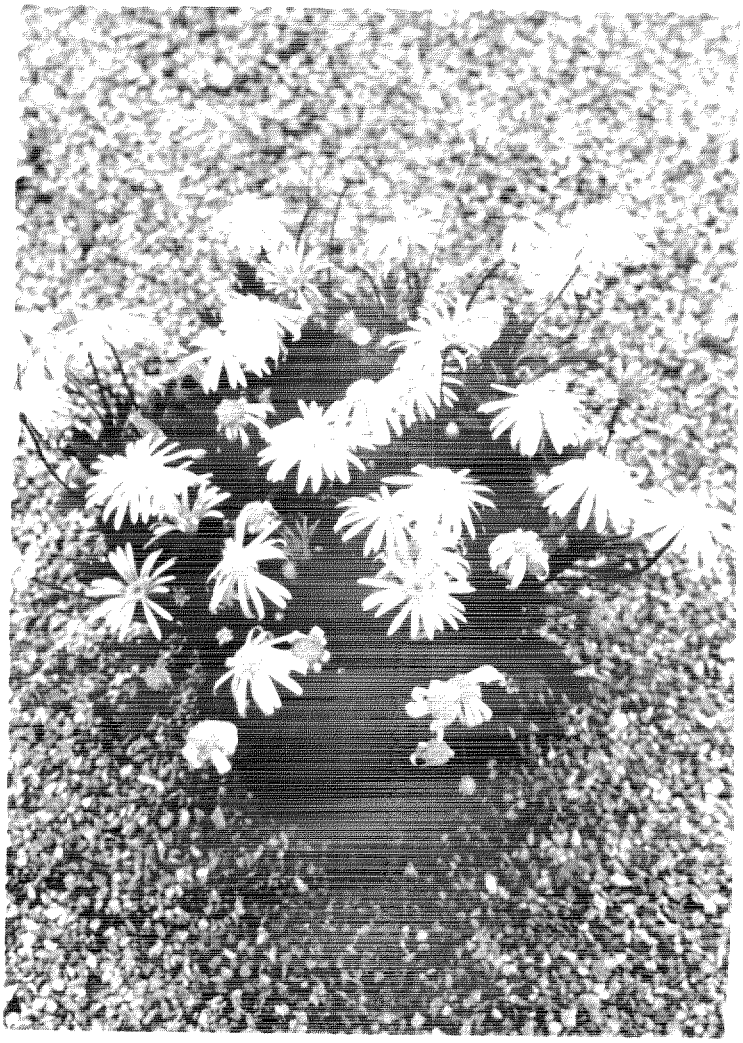
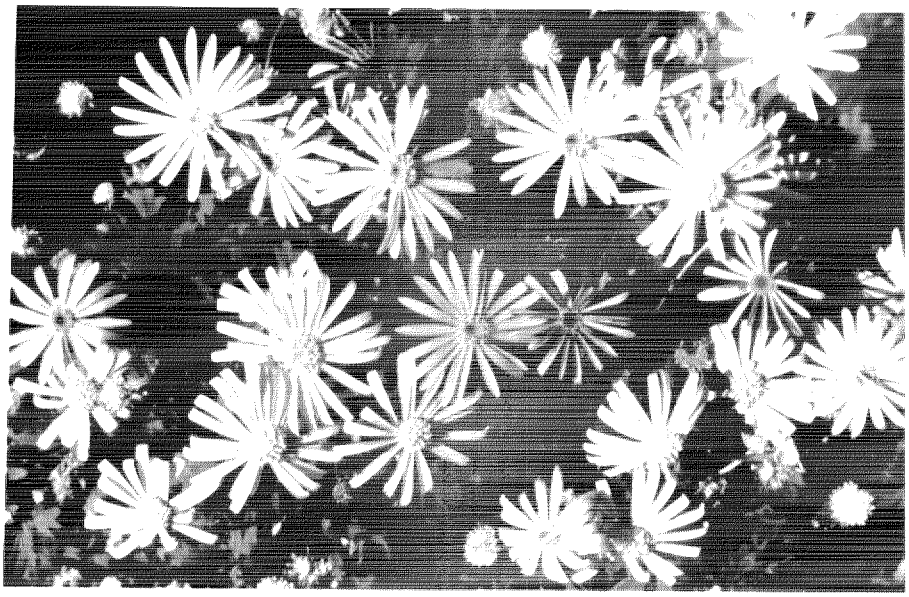

* * * * *